United States Patent [19]
van der Bruggen et al.

[11] Patent Number: 6,093,540
[45] Date of Patent: Jul. 25, 2000

[54] METHOD FOR DIAGNOSING A DISORDER CHARACTERIZED BY EXPRESSION OF A BAGE TUMOR REJECTION ANTIGEN PRECURSOR

[75] Inventors: Pierre van der Bruggen; Thierry Boon-Falleur; Pierre Coulie; Jean-Christophe Renauld, all of Brussels, Belgium

[73] Assignee: Ludwig Institute for Cancer Research, New York, N.Y.

[21] Appl. No.: 08/573,186

[22] Filed: Dec. 15, 1995

Related U.S. Application Data

[62] Division of application No. 08/079,110, Jun. 17, 1993, Pat. No. 5,571,711.

[51] Int. Cl.[7] .............................. C12Q 1/68; G01N 33/53
[52] U.S. Cl. .................. 435/6; 435/7.1; 435/7.2; 435/7.21; 435/7.24; 436/63; 436/64; 436/503
[58] Field of Search ................... 435/7.24, 6, 7.1, 435/7.2, 7.21; 436/64, 503, 63

[56] References Cited

U.S. PATENT DOCUMENTS 5,683,886  11/1997  van der Bruggen et al. .

*Primary Examiner*—Patricia A. Duffy
*Attorney, Agent, or Firm*—Fulbright & Jaworski, LLP

[57] ABSTRACT

A new family of tumor rejection antigen precursors, and the nucleic acid molecules which code for them, are disclosed. These tumor rejection antigen precursors are referred to as BAGE tumor rejection antigen precursors, and the nucleic acid molecules which code for them are referred to as BAGE coding molecules. Various diagnostic and therapeutic uses of the coding sequences and the tumor rejection antigen precursor molecules are described.

8 Claims, 3 Drawing Sheets

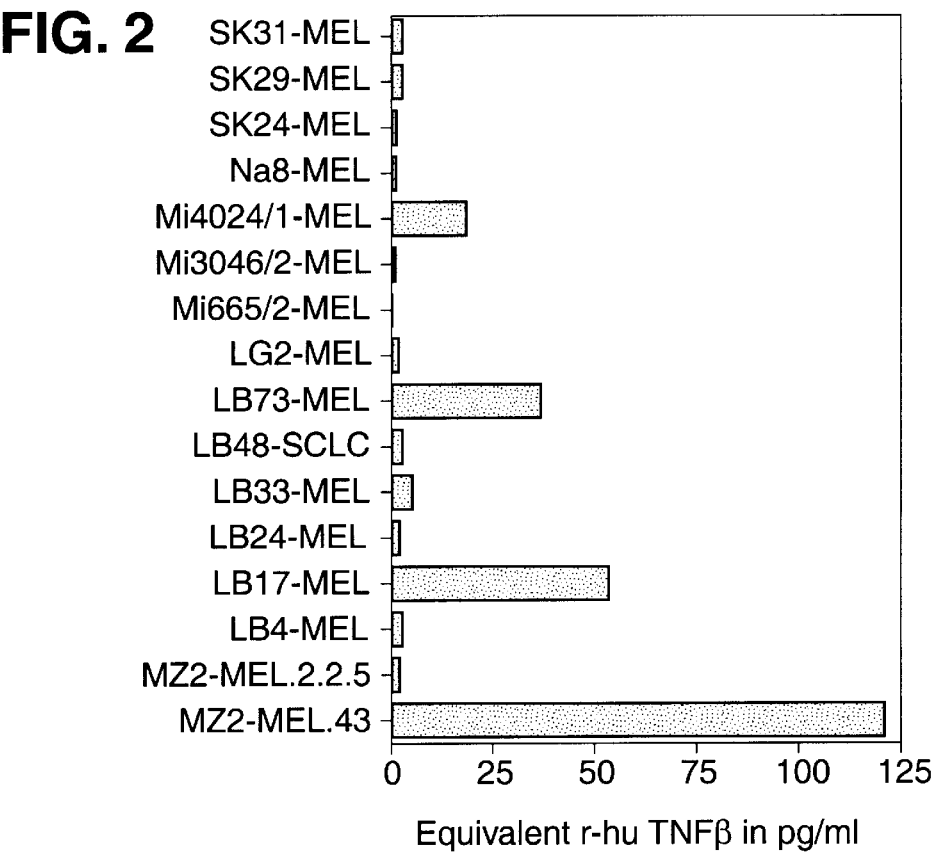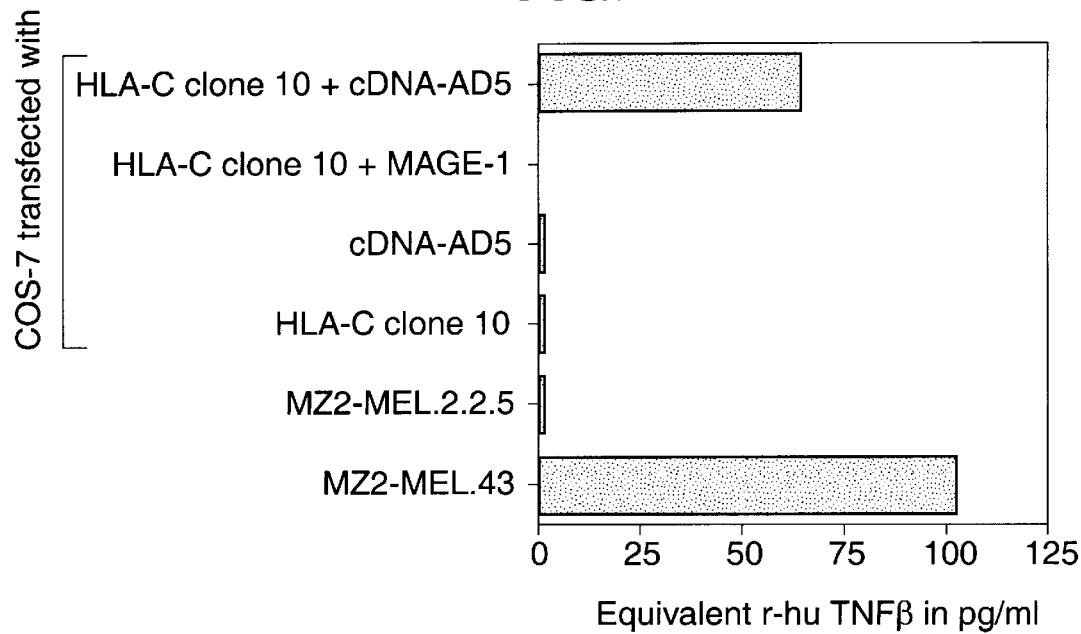

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
       (A) LENGTH: 1032 base pairs
       (B) TYPE: nucleic acid
       (C) STRANDEDNESS: single
       (D) TOPOLOGY: linear (xi) SEQUENCE DESCRIPTION: SEQ ID NO: 1:

```
CGCCAATTTA GGGTCTCCGG TATCTCCCGC TGAGCTGCTC TGTTCCCGGC TTAGAGGACC      60

AGGAGAAGGG GGAGCTGGAG GCTGGAGCCT GTAACACCGT GGCTCGTCTC ACTCTGGATG     120

GTGGTGGCAA CAGAGATGGC AGCGCAGCTG GAGTGTTAGG AGGGCGGCCT GAGCGGTAGG     180

AGTGGGGCTG GAGCAGTAAG ATGGCGGCCA GAGCGGTTTT TCTGGCATTG TCTGCCCAGC     240

TGCTCCAAGC CAGGCTGATG AAGGAGGAGT CCCCTGTGGT GAGCTGGAGG TTGGAGCCTG     300

AAGACGGCAC AGCTCTGTGC TTCATCTTCT GAGGTTGTGG CAGCCACGGT GATGGAGACG     360

GCAGCTCAAC AGGAGCAATA GGAGGAGATG GAGTTTCACT GTGTCAGCCA GGATGGTCTC     420

GATCTCCTGA CCTCGTGATC CGCCCGCCTT GGCCTTCCAA AGTGCCGAGA TTACAGCGAT     480

GTGCATTTTG TAAGCACTTT GGAGCCACTA TCAAATGCTG TGAAGAGAAA TGTACCCAGA     540

TGTATCATTA TCCTTGTGCT GCAGGAGCCG GCTCCTTTCA GGATTTCAGT CACATCTTCC     600

TGCTTTGTCC AGAACACATT GACCAAGCTC CTGAAAGATG TAAGTTTACT ACGCATAGAC     660

TTTTAAACTT CAACCAATGT ATTTACTGAA ATAACAAAT GTTGTAAATT CCCTGAGTGT      720

TATTCTACTT GTATTAAAAG GTAATAATAC ATAATCATTA AAATCTGAGG GATCATTGCC     780

AGAGATTGTT GGGGAGGGAA ATGTTATCAA CGGTTTCATT GAAATTAAAT GTTATCAACG     840

GTTTCATTGA AATTAAATCC AAAAAGTTAT TTCCTCAGAA AAATCAAATA AAGTTTGCAT     900

GTTTTTTATT CTTAAAAACAT TTTAAAAACC ACTGTAGAAT GATGTAAATA GGGACTGTGC    960

AGTATTTCTG ACATATACTA TAAAATTATT AAAAAGTCAA TCAGTATTCA ACATCTTTTA   1020

CACTAAAAAG CC                                                       1032
```

(2) INFORMATION FOR SEQ ID NO: 2:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (xi) SEQUENCE DESCRIPTION: SEQ ID NO: 2:

```
CAGAAGATGA AGCACAGAG                                                   19
```

(2) INFORMATION FOR SEQ ID NO: 3:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO: 3:

```
GAGCGGTTTT TCTGGCATTG                                                  20
```

```
(2) INFORMATION FOR SEQ ID NO: 4:

(i) SEQUENCE CHARACTERISTICS:
        (A) LENGTH:  21 base pairs
        (B) TYPE:  nucleic acid
        (C) STRANDEDNESS:  single
        (D) TOPOLOGY:  linear (xi) SEQUENCE DESCRIPTION:  SEQ ID NO: 4:

CGGCTTAGAG GACCAGGAGA A                                              21

(2) INFORMATION FOR SEQ ID NO: 5:

(i) SEQUENCE CHARACTERISTICS:
        (A) LENGTH:  20 base pairs
        (B) TYPE:  nucleic acid
        (C) STRANDEDNESS:  single
        (D) TOPOLOGY:  linear (xi) SEQUENCE DESCRIPTION:  SEQ ID NO: 5:

GGCTCCAACC TCCAGCTCAC                                                20

(2) INFORMATION FOR SEQ ID NO: 6:

(i) SEQUENCE CHARACTERISTICS:
        (A) LENGTH:  19 base pairs
        (B) TYPE:  nucleic acid
        (C) STRANDEDNESS:  single
        (D) TOPOLOGY:  linear (xi) SEQUENCE DESCRIPTION:  SEQ ID NO: 6:

TTAGAGGACC AGGAGAAGG                                                 19
```

METHOD FOR DIAGNOSING A DISORDER CHARACTERIZED BY EXPRESSION OF A BAGE TUMOR REJECTION ANTIGEN PRECURSOR

This is a Divisional Application of application Ser. No. 08/079,110, filed Jun. 17, 1993, now U.S. Pat. No. 5,571,711.

FIELD OF THE INVENTION

This invention relates to a nucleic acid molecule which codes for a tumor rejection antigen precursor. More particularly, the invention concerns genes, whose tumor rejection antigen precursor is processed, inter alia, into at least one tumor rejection antigen that is presented by HLA-C clone 10 molecules. The genes in question do not appear to be related to other known tumor rejection antigen precursor coding sequences.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., Advanced Immunology (J. P. Lipincott Company, 1987), especially chapters 6–10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also, see U.S. patent application Ser. No. 807,043, filed Dec. 12, 1991, now U.S. Pat. No. 5,342,774.

In U.S. patent application Ser. No. 938,334 now U.S. Pat. No. 5,405,940, the disclosure of which is incorporated by reference, nonapeptides are taught which are presented by the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993 now U.S. Pat. No. 5,629,166 and incorporated by reference, the fact that the MAGE-1 expression product is processed to a second TRA is disclosed. This second TRA is presented by HLA-C clone 10 molecules. The disclosure shows that a given TRAP can yield a plurality of TRAs.

In U.S. patent application Ser. No. 994,928, filed Dec. 22, 1992, and incorporated by reference herein, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

In U.S. patent application (Ser. No. 08/032,978), filed Mar. 18, 1993 now U.S. Pat. No. 5,620,886, and incorporated by reference in its entirety, a second TRA, not derived from tyrosinase is taught to be presented by HLA-A2 molecules. The TRA is derived from a TRAP, but is coded for by a non MAGE gene. This disclosure shows that a particular HLA molecule may present TRAs derived from different sources.

The work which is presented by the papers, patent, and patent applications cited supra deals, in large part, with the MAGE family of genes. It has now been found, however, that additional tumor rejection antigen precursors are expressed by cells. These tumor rejection antigen precursors are referred to as "BAGE" tumor rejection antigen precursors. They do not show homology to the MAGE family of genes. Thus the invention relates to genes encoding such TRAPs, the tumor rejection antigen precursors themselves as well as applications of both.

The invention is elaborated upon further in the disclosure which follows.

BRIEF DESCRIPTION OF THE FIGURES

FIG. 2 shows the results of a TNF release assay when CTL clone 82/82 was used against a panel of different cell lines.

FIG. 4 presents the results of a test of various transfectants using CTL clone 82/82, and measuring TNF release.

DETAILED DESCRIPTION OF PREFERRED EMBODIMENTS

EXAMPLE 1

A melanoma cell line, MZ2-MEL was established from melanoma cells taken from patient MZ2, using standard methodologies. This cell line is described, e.g., in PCT Application PCT/US92/04354, filed May 22, 1992, published Nov. 26, 1992, and incorporated by reference in its entirety. Once the cell line was established, a sample thereof was irradiated, so as to render it non-proliferative. These irradiated cells were then used to isolate cytolytic T cell clones ("CTLs") specific thereto.

A sample of peripheral blood mononuclear cells ("PBMCs") was taken from patient MZ2, and contacted to the irradiated melanoma cells. The mixture was observed for lysis of the melanoma cells, which indicated that CTLs specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS, and incubated for 45 minutes at 37° C. with 200 µCi/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. Samples of PBLs were added in 100 ul of the same medium, and assays were carried out in duplicate. Plates were centrifuged for 4 minutes at 100 g, and incubated for four hours at 37° C. in a 8% CO$_2$ atmosphere.

Plates were centrifuged again, and 100 ul aliquots of supernatant were collected and counted. Percentage of $^{51}$Cr release was calculated as follows:

$$\%^{51}Cr \text{ release} = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology. The CTL clone MZ2-CTL 82/82 was thus isolated. The clone is referred to as "82/82" hereafter.

Figure 1B:
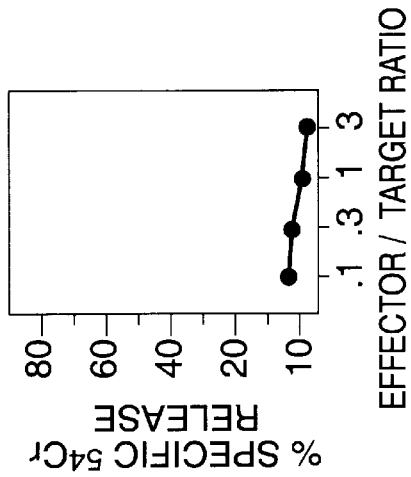
FIG. 1 sets forth the results of a chromium release assay using CTL clone 82/82 against various cell lines.
Figure 1D:
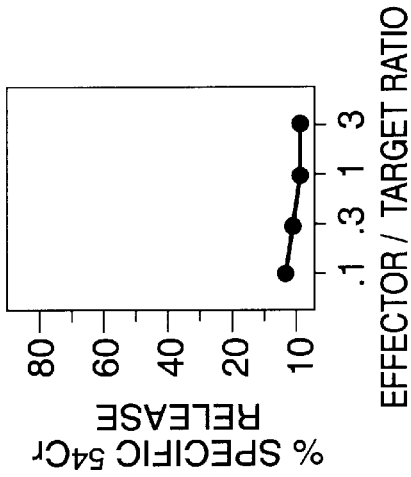
Figure 1A:
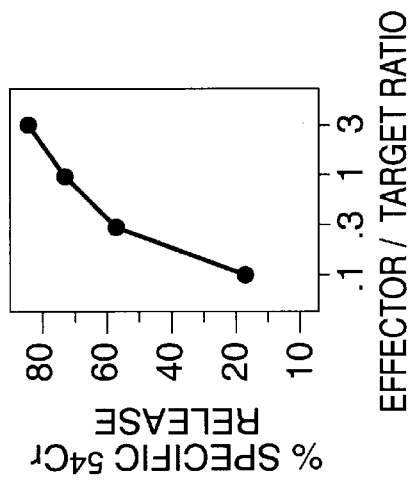
Figure 1C:
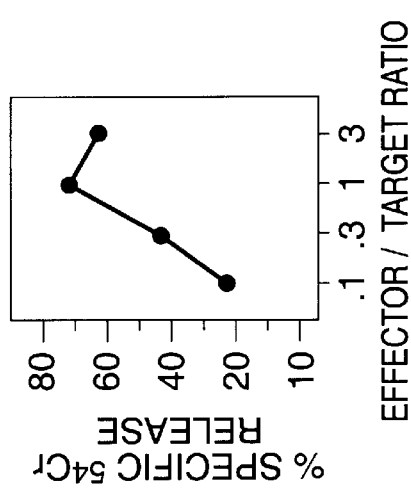

The same method was used to test target K562 cells, as well as a melanoma cell line. These results, presented in FIG. 1A, show that this CTL clone recognizes and lyses the melanoma cell line, but not K562. The CTL clone, 82/82, was then tested against melanoma cell lines in the same manner described supra. FIG. 1 shows that, while MZ2-MEL.43 is lysed by CTL clone 82/82, the cell line MZ2-MEL 2.2.5, a variant which has lost expression of HLA-A29, HLA-B44, and HLA-C clone 10 is not, suggesting that the TRA is presented by one of these HLA molecules. When cell line MZ2-MEL 2.2.5 was transfected with DNA coding for HLA-C clone 10, using well known techniques, the cells became sensitive to lysis by CTL clone 82/82, thus demonstrating that the antigen recognized by CTL clone 82/82 is presented by HLA-C clone 10.

EXAMPLE 2

Further studies were carried out to determine if 82/82 also produced tumor necrosis factor ("TNF") when contacted with target cells. The method used was that described by Traversari et al., Immunogenetics 35: 145–152 (1992), the disclosure of which is incorporated by reference. Briefly, samples of the CTL line were combined with samples of a target cell of interest, in culture medium. After 24 hours, supernatant from the cultures was removed, and then tested on TNF sensitive WEHI cells. A panel of fourteen different cell lines were tested, as shown in FIG. 2.

The results, presented in terms of the percentage of WEHI cells which died upon exposure to the supernatant, are shown in FIG. 2. The results demonstrate that three melanoma cell lines present this antigen. As a result of the strong response by MZ2 MEL43, it was used in the experiments which follow.

EXAMPLE 3

The results from Example 2 indicated that MZ2.MEL.43 presented the target antigen of interest. As such, it was used as a source of total mRNA to prepare a cDNA library.

Total RNA was isolated from the cell line. The mRNA was isolated using an oligo-dT binding kit, following well recognized techniques. Once the mRNA was secured, it was transcribed into cDNA, again using standard methodologies. The cDNA was then ligated to EcoRI adaptors and cloned into the EcoRI site of plasmid pcD-SRα, in accordance with the manufacturer's instructions. The recombinant plasmids were then electroporated into JM101 *E. coli* (electroporation conditions: 1 pulse at 25 µfarads, 2500 V).

The transfected bacteria were selected with ampicillin (50 µg/ml), and then divided into 87 pools of 400 bacteria and 297 pools of 200 bacteria. Each pool represented either about 280 or about 140 cDNAs, as analysis showed that about 70% of plasmids contained an insert. Each pool was amplified to saturation, and plasmid DNA was isolated via alkaline lysis, potassium acetate precipitation without phenol extraction, following Maniatis et al., in Molecular Cloning: A Laboratory Manual (Cold Spring Harbor, N.Y., 1982).

EXAMPLE 4

Following preparation of the library described in Example 3, the cDNA was transfected into eukaryotic cells. The transfections, described herein, were carried out in duplicate. Samples of COS-7 cells were seeded, at 15,000 cells/well into tissue culture flat bottom microwells, in Dulbeco's modified Eagles Medium ("DMEM") supplemented with 10% fetal calf serum. The cells were incubated overnight at 37° C., medium was removed and then replaced by 50 µl/well of DMEM medium containing 10% Nu serum, 400 µg/ml DEAE-dextran, and 100 µM chloroquine, plus 100 ng of subject plasmids. These plasmids were the plasmids of the various pools described supra, and 100 ng of plasmids containing DNA coding for HLA-C clone 10 in plasmid pcD-SRα. Following four hours of incubation at 37° C., the medium was removed, and replaced by 50 µl of PBS containing 10% DMSO. This medium was removed after two minutes and replaced by 200 µl of DMEM supplemented with 10% FCS.

Following this change in medium, COS cells were incubated for 24–48 hours at 37° C. Medium was then discarded, and 1500 cells of CTL clone 82/82 were added, in 100 µl of Iscove medium containing 10% pooled human serum supplemented with 20 U/ml of IL-2. Supernatant was removed after 24 hours, and TNF content was determined in an assay on WEHI cells, as described by Traversari et al., Immunogenetics 35: 145–152 (1992), the disclosure of which is incorporated by reference.

Figure 3:
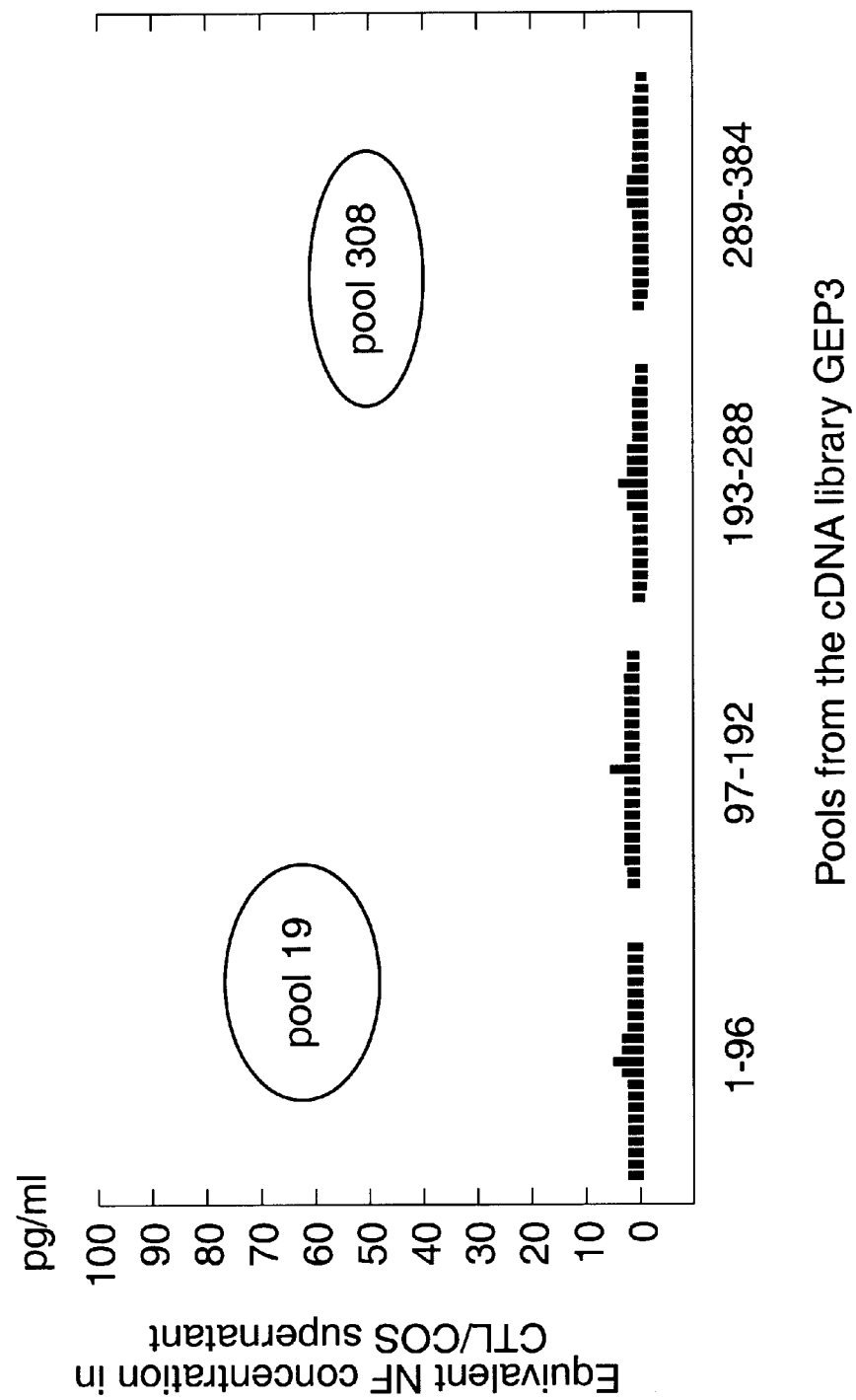
FIG. 3 depicts the results of a TNF release assay using transfected COS cells.

Of the 384 pools tested, 99% stimulated TNF, at a concentration below 5 pg/ml. Two pools gave concentrations above 40 pg/ml, with duplicate wells giving equivalent results. FIG. 3 shows this. The bacteria from one of these pools, i.e., pool 19, were selected for further experiments.

EXAMPLE 5

The bacteria of pool 19 were cloned, and 800 bacteria were tested. Plasmid DNA was extracted therefrom, transfected into a new sample of COS cells in the same manner as described supra, and the cells were again tested for stimulation of CTL clone 82/82. Twelve positive clones were found. One of these, referred to as cDNA clone AD5 was tested further. In a comparative test COS cells were transfected with cDNA clone AD5 and the HLA-C clone 10. HLA-C clone 10 and MAGE-1, AD5 alone, or HLA-C clone 10 alone. Control cell lines MZ2-MEL 2.2.5 and MZ2-MEL.43 were also used. TNF release in CTL supernatant was measured by testing it on WEHI cells, as referred to supra. The optical density of the surviving WEHI cells was measured using MTT. FIG. 4 shows that only the COS cells transfected with HLA-C clone 10 and cDNA-AD5, and the original cell line MZ2-MEL 43 stimulated TNF release from CTL clone 82/82.

EXAMPLE 6

The cDNA AD5 was sequenced following art known techniques. A sequence search revealed that the plasmid insert showed no homology to known genes or proteins. SEQUENCE ID NO: 1 presents cDNA nucleotide information for the identified gene, referred to hereafter as "BAGE-1". A putative open reading frame is located at bases 201–332 of the molecule.

EXAMPLE 7

Following the sequencing of the cDNA, as per example 6, experiments were carried out to determine if cells of normal tissues expressed the gene. To determine this, RNA isolated from normal tissues was reverse transcribed, using oligo-dT as primer. The resulting cDNA was then amplified, using primers:

5' CAG AAG ATG AAG CAC AGA G-3' (SEQ ID NO:2)
and
5'-GAG CGG TTT TTC TGG CAT TG-3' (SEQ ID NO:3)
and standard PCR methodologies. Radioactive nucleotides were added so that the amount of amplification product could be determined via phosphor imaging.

The amount of product was expressed as a percentage of the product secured from cell line MZ2-MEL 3.0, which was shown to express the gene. The results are as follows:

| MZ2-MEL 3.0 | 100% |
|---|---|
| Lung | <0.5% |
| Breast | " |
| Stomach | " |
| Skin | " |
| Brain | " |
| Prostate | " |
| Kidney | " |
| Testis | 8% |

In additional experiments not elaborated upon herein, the DNA of cell line MZ2-MEL was digested with EcoRI, and then hybridized with a PCR probe corresponding to the first 300 nucleotides of the cDNA described herein. Following standard Southern blotting, four bands, corresponding to sizes of approximately 5.8, 7.5, 8.5 and 11 kilobases were identified, suggesting the existence of a family of Bage genes.

EXAMPLE 8

Expression of the gene by tumor samples and tumor cell lines was also determined. cDNA was secured just as in example 4, and then nested primer methodologies were carried out to amplify the pertinent sequences. First, twenty cycles of amplification were carried out, using primers:

5'-CGG CTT AGA GGA CCA GGA GAA-3' (SEQ ID NO:4)
and
5'CAG AAG ATG AAG CAC AGA G-3' (SEQ ID NO:2)
This was followed by twenty additional cycles using primers:

5'-GGC TCC AAC CTC CAG CTC AC-3' (SEQ ID NO:5)
AND
5'-TTA GAG GAC CAG GAG AAG G-3' (SEQ ID NO:6)
The results are presented below. The first figure is the number of positive samples; the second is the total number of samples tested:

| Melanoma | 12/20 |
|---|---|
| Breast Carcinoma | 2/5 |
| Small Cell lung carcinoma | 2/8 |
| Non-small cell lung carcinoma | 2/5 |
| Sarcoma | 1/4 |
| Head and neck tumors | 1/6 |
| Colon carcinoma | 0/4 |
| Kidney tumor | 0/5 |
| Leukemia/Lymphoma | 0/3 |

The foregoing examples show the isolation of a nucleic acid molecule which codes for a tumor rejection antigen precursor. This "TRAP" coding molecule, however, is not homologous with any of the previously disclosed MAGE coding sequences described in the references set forth supra. Hence, one aspect of the invention is an isolated nucleic acid molecule which comprises the nucleotide sequence set forth in SEQ ID NO: 1. This sequence is not a MAGE coding sequence, as will be seen by comparing it to the sequence of any of the MAGE genes described in the references. Also a part of the invention are those nucleic acid sequences which also code for a non-MAGE tumor rejection antigen precursor but which hybridize to a nucleic acid molecule containing the described nucleotide sequence, under stringent conditions. The term "stringent conditions" as used herein refers to parameters with which the art is familiar. More specifically, stringent conditions, as used herein, refers to hybridization in 3.5×SSC, 1×Denhardt's solution, 25 mM sodium phosphate buffer (pH 7.0), 0.5% SDS, and 2 mM EDTA for 18 hours at 65° C. This is followed by four washes of the filter, at 65° C. for 20 minutes, in 2×SSC, 0.1% SDS, and one wash for up to 20 minutes in 0.3×SSC, 0.1% SDS. There are other conditions, reagents, and so forth which can be used, which result in the same degree of stringency. The skilled artisan will be familiar with such conditions, and thus they are not given here.

It will also be seen from the examples that the invention embraces the use of the sequences in expression vectors, as well as to transfect host cells and cell lines, be these prokaryotic (e.g., E. coli), or eukaryotic (e.g., CHO or COS cells). The expression vectors require that the pertinent sequence, i.e., those described supra, be operably linked to a promoter. As it has been found that human leukocyte antigen HLA-C clone 10 presents a tumor rejection antigen derived from these genes, the expression vector may also include a nucleic acid sequence coding for HLA-C clone 10. In a situation where the vector contains both coding sequences, it can be used to transfect a cell which does not normally express either one. The tumor rejection antigen precursor coding sequence may be used alone, when, e.g., the host cell already expresses HLA-C clone 10. Of course, there is no limit on the particular host cell which can be used. As the vectors which contain the two coding sequences may be used in HLA-C clone 10 presenting cells if desired, and the gene for tumor rejection antigen precursor can be used in host cells which do not express HLA-C clone 10.

The invention also embraces so called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

To distinguish the nucleic acid molecules and the TRAPs of the invention from the previously described MAGE family, the invention shall be referred to as the BAGE family of genes and TRAPs. Hence, whenever "BAGE" is used herein, it refers to the tumor rejection antigen precursors coded for by the previously described sequences. "BAGE coding molecule" and similar terms, are used to describe the nucleic acid molecules themselves.

The invention as described herein has a number of uses, some of which are described herein. First, the invention permits the artisan to diagnose a disorder characterized by expression of the TRAP. These methods involve determining expression of the TRAP gene, and/or TRAs derived therefrom, such as a TRA presented by HLA-C clone 10. In the former situation, such determinations can be carried out via any standard nucleic acid determination assay, including the polymerase chain reaction, or assaying with labelled hybridization probes. In the latter situation, assaying with binding partners for complexes of TRA and HLA, such as antibodies, is especially preferred. An alternate method for determination is a TNF release assay, of the type described supra.

The isolation of the TRAP gene also makes it possible to isolate the TRAP molecule itself, especially TRAP molecules containing the amino acid sequence coded for by SEQ ID NO: 1. These isolated molecules when presented as the TRA, or as complexes of TRA and HLA, such as HLA-C clone 10, may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to prove a CTL response, or be cells which express both molecules without transfection. Further, the TRAP molecule, its associated TRAs, as well as complexes of TRA and HLA, may be used to produce antibodies, using standard techniques well known to the art.

When "disorder" is used herein, it refers to any pathological condition where the tumor rejection antigen precursor is expressed. An example of such a disorder is cancer melanoma in particular.

Therapeutic approaches based upon the disclosure are premised on a response by a subject's immune system, leading to lysis of TRA presenting cells, such as HLA-c clone 10 cells. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5): 1917 (1986); Reddel et al., Science 257: 238 (Jul. 10, 1992); Lynch et al., Eur. J. Immunol. 21: 1403–1410 (1991); Kast et al., Cell 59: 603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case a BAGE sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a BAGE derived, tumor rejection antigen is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining the tumor rejection antigen or the precursor itself with an adjuvant to facilitate incorporation into HLA-C clone 10 presenting cells which present the HLA molecule of interest. The TRAP is processed to yield the peptide partner of the HLA molecule while the TRA is presented without the need for further processing.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Method for screening for possibility of a disorder characterized by expression of a BAGE tumor rejection antigen precursor which is processed to a BAGE derived tumor rejection antigen which forms a complex with HLA-C clone 10 molecules, comprising contacting a sample from a subject with an antibody specific for said complex and determining interaction between said complex and said antibody as a determination of possible presence of said disorder.

2. Method for screening for possibility of a disorder characterized by expression of a tumor rejection antigen precursor coded for by a nucleic acid molecule having the sequence set forth in SEQ ID NO: 1 comprising contacting a sample from a subject with an agent specific for said sequence or an expression product thereof, and determining interaction between said agent and said sequence or said expression product as a determination of possible presence of said disorder.

3. The method of claim 2, wherein said agent is an antibody for said expression product.

4. The method of claim 2, wherein said agent comprises at least one oligonucleotide specific for said sequence.

5. The method of claim 4, wherein said method is a polymerase chain reaction.

6. The method of claim 5, wherein said agent comprises at least two oligonucleotides.

7. The method of claim 6, wherein said two oligonucleotides are SEQ ID NO:2 and SEQ ID NO:3.

8. The method of claim 6, wherein said oligonucleotides are SEQ ID NO:2, SEQ ID NO:3, SEQ ID NO:5, and SEQ ID NO:6.

* * * * *